(12) United States Patent  (10) Patent No.: US 9,717,424 B2
Kulach  (45) Date of Patent: Aug. 1, 2017

(54) SYSTEM AND METHOD FOR GENERATING A PPG SIGNAL

(71) Applicant: Garmin Switzerland GmbH, Schaffhausen (CH)

(72) Inventor: Christopher J. Kulach, Calgary (CA)

(73) Assignee: Garmin Switzerland GmbH (CH)

( * ) Notice: Subject to any disclaimer, the term of this patent is extended or adjusted under 35 U.S.C. 154(b) by 0 days.

(21) Appl. No.: 15/296,938

(22) Filed: Oct. 18, 2016

(65) Prior Publication Data

US 2017/0105638 A1  Apr. 20, 2017

Related U.S. Application Data

(60) Provisional application No. 62/243,447, filed on Oct. 19, 2015.

(51) Int. Cl.
*A61B 5/02* (2006.01)
*A61B 5/024* (2006.01)
(Continued)

(52) U.S. Cl.
CPC ........ *A61B 5/02416* (2013.01); *A61B 5/1112* (2013.01); *A61B 5/1118* (2013.01); *A61B 5/7278* (2013.01); *A61B 5/7285* (2013.01)

(58) Field of Classification Search
None
See application file for complete search history.

(56) References Cited

U.S. PATENT DOCUMENTS 4,258,719 A * 3/1981 Lewyn ............... A61B 5/02416
307/650
5,277,181 A * 1/1994 Mendelson ........ A61B 5/14551
356/41
(Continued)

FOREIGN PATENT DOCUMENTS

EP          0319160 A1 *  6/1989
WO     WO2006/067690 A2    6/2006
(Continued)

OTHER PUBLICATIONS

U.S. Appl. No. 15/296,956, filed Oct. 18, 2016.

*Primary Examiner* — Brian T Gedeon
(74) *Attorney, Agent, or Firm* — Samuel M. Korte; Max M. Ali

(57) ABSTRACT

Characterization of a fitness monitor based on its operation enables a processor to account for variations in device operating modes and biometric characteristics of the user. The fitness monitor includes an emitter (e.g., LED) for transmitting light toward skin of the user, a receiver (e.g., photodiode) for receiving a reflection of the transmitted light, a photometric front end for generating a photoplethysmogram (PPG) signal based on the received reflection, and a processor configured to select an intensity level for the emitter based on a comparison of a determined component of the PPG signal and a reference value. The reference value, which may characterize the fitness monitor based on a determined variability or range of the PPG signal, may be utilized by the processor to improve or maintain the signal quality of the PPG signal to enable determination of a cardiac component and/or reduction of power consumption by the fitness device.

20 Claims, 8 Drawing Sheets

(51) Int. Cl.
*A61B 5/11* (2006.01)
*A61B 5/00* (2006.01)

(56) References Cited

U.S. PATENT DOCUMENTS

| | | | | |
|---|---|---|---|---|
| 6,178,343 | B1 | 1/2001 | Bindszus | 600/323 |
| 6,702,752 | B2 | 3/2004 | Dekker | 600/484 |
| 6,997,879 | B1 | 2/2006 | Turcott | 600/507 |
| 7,035,679 | B2 | 4/2006 | Addison | 600/323 |
| 7,169,110 | B2* | 1/2007 | Lee | A61B 5/14551 |
| | | | | 600/481 |
| 7,215,987 | B1* | 5/2007 | Sterling | A61B 5/14551 |
| | | | | 600/322 |
| 7,336,982 | B2 | 2/2008 | Yoo | 600/323 |
| 7,470,234 | B1 | 12/2008 | Elhag | 600/485 |
| 7,625,344 | B1 | 12/2009 | Brady | 600/485 |
| 7,729,748 | B2 | 6/2010 | Florian | 600/476 |
| 7,794,406 | B2* | 9/2010 | Reisfeld | A61B 5/0402 |
| | | | | 600/479 |
| 7,867,142 | B2 | 1/2011 | Kim | 482/8 |
| 8,109,874 | B2 | 2/2012 | Kong | 600/300 |
| 8,251,903 | B2 | 8/2012 | LeBoeuf et al. | 600/309 |
| 8,260,405 | B2 | 9/2012 | Aarts | 600/509 |
| 8,460,199 | B2 | 6/2013 | Rulkov | 600/503 |
| 8,463,347 | B2 | 6/2013 | Watson | 600/324 |
| 8,509,882 | B2 | 8/2013 | Albert | 600/509 |
| 8,512,242 | B2 | 8/2013 | LeBoeuf et al. | 600/309 |
| 8,554,297 | B2* | 10/2013 | Moon | A61B 5/746 |
| | | | | 600/310 |
| 8,591,411 | B2 | 11/2013 | Banet | 600/300 |
| 8,647,270 | B2 | 2/2014 | LeBoeuf et al. | 600/301 |
| 8,652,040 | B2 | 2/2014 | LeBoeuf et al. | 600/301 |
| 8,670,123 | B2 | 3/2014 | Schleipen | 356/445 |
| 8,700,111 | B2 | 4/2014 | LeBoeuf et al. | 600/310 |
| 8,788,002 | B2 | 7/2014 | LeBoeuf et al. | 600/310 |
| 8,827,906 | B2 | 9/2014 | Yuen | 600/301 |
| 8,886,269 | B2 | 11/2014 | LeBoeuf et al. | 600/310 |
| 8,888,701 | B2 | 11/2014 | LeBoeuf et al. | 600/300 |
| 8,923,941 | B2 | 12/2014 | LeBoeuf et al. | 600/310 |
| 8,929,965 | B2 | 1/2015 | LeBoeuf et al. | 600/310 |
| 8,929,966 | B2 | 1/2015 | LeBoeuf et al. | 600/310 |
| 8,934,952 | B2 | 1/2015 | LeBoeuf et al. | 600/310 |
| 8,942,776 | B2 | 1/2015 | LeBoeuf et al. | 600/310 |
| 8,945,017 | B2 | 2/2015 | Venkatraman | 600/500 |
| 8,954,135 | B2 | 2/2015 | Yuen | 600/476 |
| 8,974,396 | B1* | 3/2015 | Brady | A61B 5/02416 |
| | | | | 600/508 |
| 8,989,830 | B2 | 3/2015 | LeBoeuf et al. | 600/310 |
| 8,998,815 | B2 | 4/2015 | Venkatraman | 600/300 |
| 9,005,129 | B2 | 4/2015 | Venkatraman | 600/300 |
| 9,014,790 | B2* | 4/2015 | Richards | A61B 5/02438 |
| | | | | 600/473 |
| 9,039,614 | B2 | 5/2015 | Yuen | |
| 9,044,171 | B2 | 6/2015 | Venkatraman | 342/357.74 |
| 9,044,180 | B2 | 6/2015 | LeBoeuf et al. | 600/310 |
| 9,131,312 | B2 | 9/2015 | LeBoeuf et al. | |
| 9,289,135 | B2 | 3/2016 | LeBoeuf et al. | 600/310 |
| 9,289,175 | B2 | 3/2016 | LeBoeuf et al. | 600/310 |
| 9,301,696 | B2 | 4/2016 | LeBoeuf et al. | 600/310 |
| 9,307,917 | B2 | 4/2016 | Hong et al. | |
| 9,314,167 | B2 | 4/2016 | LeBoeuf et al. | 600/310 |
| 9,538,921 | B2 | 1/2017 | LeBoeuf et al. | |
| 2005/0143665 | A1 | 6/2005 | Huiku | 600/500 |
| 2009/0048526 | A1 | 2/2009 | Aarts | 600/508 |
| 2009/0105556 | A1 | 4/2009 | Fricke | 600/301 |
| 2009/0259116 | A1* | 10/2009 | Wasserman | A61B 5/14551 |
| | | | | 600/323 |
| 2010/0113948 | A1 | 5/2010 | Yang | 600/500 |
| 2011/0054277 | A1* | 3/2011 | Pinter | A61B 5/0205 |
| | | | | 600/324 |
| 2011/0082355 | A1 | 4/2011 | Eisen | 600/324 |
| 2012/0197137 | A1 | 8/2012 | Jeanne | 600/479 |
| 2013/0231926 | A1 | 9/2013 | Gigi | 704/207 |
| 2013/0261415 | A1* | 10/2013 | Ashe | A61B 5/14552 |
| | | | | 600/324 |
| 2014/0213858 | A1 | 7/2014 | Presura | 600/301 |
| 2014/0276099 | A1 | 9/2014 | Kirenko | 600/476 |
| 2014/0288436 | A1 | 9/2014 | Venkatraman | 600/479 |
| 2014/0316305 | A1 | 10/2014 | Venkatraman | 600/595 |
| 2015/0173628 | A1 | 6/2015 | Yuen | |
| 2015/0196256 | A1 | 7/2015 | Venkatraman | |
| 2016/0235313 | A1* | 8/2016 | Sharma | A61B 5/02427 |

FOREIGN PATENT DOCUMENTS

| | | |
|---|---|---|
| WO | WO2011/051888 A2 | 5/2011 |
| WO | WO2013/042070 A1 | 3/2013 |
| WO | WO2013/124750 A1 | 8/2013 |
| WO | WO2013/190423 A1 | 12/2013 |

* cited by examiner

SYSTEM AND METHOD FOR GENERATING A PPG SIGNAL

CROSS-REFERENCE TO RELATED APPLICATIONS

This patent application claims priority benefit under 35 U.S.C. §119(e), with regard to all common subject matter, of U.S. Provisional Application Ser. No. 62/243,447, filed Oct. 19, 2015, titled "PPG SIGNAL ANALYSIS," which is hereby incorporated by reference in its entirety. This application is related to simultaneously filed U.S. patent application Ser. No. 15/296,956, entitled "HEART RATE MONITOR WITH TIME-VARYING LINEAR FILTERING", the entire contents of which is expressly incorporated herein.

BACKGROUND

A photoplethysmogram (PPG) signal is commonly utilized to monitor physiological metrics of an individual, such as cardiac information, for example, a heartbeat signal or a heart-rate. Devices that generate a PPG signal using optical techniques typically include an emitter configured to output light toward skin of the user and a receiver, which may include a photodiode and electrical circuitry, configured to generate a light intensity signal based on a light reflections received by the photodiode and using the electrical circuitry to generate a PPG signal based on the light intensity signal. The PPG signal typically includes a cardiac component, a motion component, a respiratory component and other components may be included as well.

To effectively monitor the physiological characteristic, several factors that may adversely affect the measurement of the physiological characteristic are generally considered. For example, a PPG signal quality for a desired cardiac component of the PPG signal is sensitive to variations in operating parameters of the device and biometric characteristics of the user (e.g., skin tone or complexion, skin density, body fat of the user, moisture level of the user's skin, hair density or color, etc.) at a location on the user's body (e.g., the user's wrist) against which the monitoring device is positioned to output light and receive reflections (e.g., output to and received from the skin on the top of the user's wrist). Operating parameters of the device may include a particular gain setting, number of channels for one or more photodiodes, a number of pulses of light output by one or more emitters (LEDs), a width of each pulse output by the one or more emitters (LEDs), a voltage of the one or more emitters (LEDs), or a current of the one or more emitters (LEDs). These variations may rapidly degrade the signal-to-noise ratio (SNR) for the cardiac component of the PPG signal and adversely impact the accuracy of measurements. Additionally, the components utilized to perform the measurements have an inherent range of operating characteristics that may affect the accuracy of the monitoring device.

Known techniques for accounting for certain variations of amongst users of fitness monitors includes characterizing the user by determining mathematical relationships for each user while the device is in use. For example, a fitness monitor may operate in a first mode to measure a heart rate by using light pulses of constant intensity and a characterization mode to determine a relationship between varying intensity levels of light and collected data points. For instance, the characterization mode may include varying the intensity of a light source, measuring light reflected to a photodiode and determining a relationship between the collected data points and the varying levels of light. It is therefore desired to provide a monitoring device, for example, a fitness monitor device, that characterizes the fitness monitor instead of characterizing the user while the device is in use. Characterization of a fitness monitor based on its operation enables the fitness monitor to account for variations in operating parameters of the device and biometric characteristics of the user without utilizing a characterization mode.

SUMMARY

In one aspect of the invention, a fitness monitor attached to a user for monitoring a cardiac signal of the user includes an emitter configured to output light toward skin of the user, an emitter driver configured to cause the emitter to output light at one of a plurality of intensity levels, a receiver configured to receive a reflection of the transmitted light and generate a light intensity signal based on the received reflection, a photometric front end configured to receive the light intensity signal and generate a photoplethysmogram (PPG) signal based on the light intensity signal, the PPG signal including a cardiac signal, and a memory device configured to store a reference value based on the variability of the PPG signal output from the photometric front end during idle operation. The fitness monitor may further include a processor communicatively coupled to the emitter, the emitter driver, the receiver, photometric front end, and the memory device, wherein the processor is configured to select a first intensity level for the emitter to output light, transmit a first output control signal including the selected first intensity level to the emitter driver causing the emitter to output light at the selected first intensity level, determine a DC component of the PPG signal, select a second intensity level based on a comparison of the determined DC component of the PPG signal with the stored reference value, transmit a second output control signal including the selected second intensity level to the emitter driver causing the emitter to output light at the selected second intensity level, and identify the cardiac component in the PPG signal.

Another aspect of the invention is directed to a fitness monitor for monitoring a cardiac signal of a user, wherein the fitness monitor includes an emitter configured to output light toward skin of the user, an emitter driver configured to cause the emitter to output light at one of a plurality of intensity levels, a receiver configured to receive a reflection of the transmitted light and generate a light intensity signal based on the received reflection, a photometric front end configured to receive the light intensity signal and generate a photoplethysmogram (PPG) signal based on the light intensity signal, the PPG signal including a cardiac signal, a reference value based on the variability of the PPG signal output from the photometric front end when the fitness monitor is not proximate to the skin of the user and a memory device configured to store the reference value. The fitness monitor further includes a processor communicatively coupled to the emitter, the receiver, photometric front end and the memory device, the processor configured to select a first intensity level for the emitter to output light, transmit a first output control signal including the selected first intensity level to the emitter driver causing the emitter to output light at the selected first intensity level, determine a DC component of the PPG signal, select a second intensity level based on a comparison of the determined DC component of the PPG signal with the stored reference value, transmit a second output control signal including the selected second intensity level to the emitter driver causing the emitter to output light at the selected second intensity level, and identify the cardiac component in the PPG signal.

In a further aspect of the invention, a fitness monitor for monitoring a cardiac signal of a user includes an emitter configured to output light toward skin of the user, an emitter driver configured to cause the emitter to output light at one of a plurality of intensity levels, a receiver configured to receive a reflection of the transmitted light and generate a light intensity signal based on the received reflection, a photometric front end configured to receive the light intensity signal and generate a photoplethysmogram (PPG) signal based on the light intensity signal and representing the cardiac signal, and a tangible non-transitory computer-readable medium storing instructions and a reference value based on the variability of the PPG signal output from the photometric front end during idle operation, wherein the instructions, when executed by one or more processors, cause the fitness monitor to select a first intensity level for the emitter to output light, transmit a first output control signal including the selected first intensity level to the emitter driver causing the emitter to output light at the selected first intensity level, determine a DC component of the PPG signal, select a second intensity level based on a comparison of the determined DC component of the PPG signal with the stored reference value, transmit a second output control signal including the selected second intensity level to the emitter driver causing the emitter to output light at the selected second intensity level, and identify the cardiac component in the PPG signal.

Many of the inventive principles and much of the inventive functionality may be implemented with or in software programs or instructions and integrated circuits (ICs) such as application specific ICs. It is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation. Therefore, in the interest of brevity and minimization of any risk of obscuring the principles and concepts in accordance to the present invention, further discussion of such software and ICs, if any, is limited to the essentials with respect to the principles and concepts of the described embodiments.

DETAILED DESCRIPTION

Aspects of the present invention enable the monitoring device, e.g., a fitness monitor, to generate a PPG signal having enhanced signal quality and/or reduced power consumption based on operation of the monitoring device during idle operation, such as when the monitoring device is not proximate to the skin of a user. Idle operation refers to the operation of the monitoring device in an environment that enables characterization of the monitoring device based on inherent operating characteristics of components implemented within a monitoring device used to measure physiological characteristics of an individual in one or more configurations or operating parameters of the monitor device. For example, characterization of the monitoring device may occur during idle operation, which may occur at a time the monitoring device is manufactured, when one or more components of the monitoring device are configured to operate in a predetermined configuration and the device is not worn by a user.

Characterization of the monitoring device prior to its use by a user may enable a processor of the monitoring device to dynamically account for variations in operating parameters of the device and biometric characteristics of the user without utilizing an operating mode that characterizes the user while the device is worn by the user, such as by outputting light in predetermined intensities and/or patterns to determine signal quality of a PPG signal generated based on reflections of the outputted light. The biometric characteristics of a user may include a skin tone or complexion of the user, the user's skin density, body fat of the user, moisture level of the user's skin, or the hair density or color of the user, at a location on the user's body against which the monitoring device is positioned to output light and receive reflections.

The monitoring device may include a receiver, which may include one or more photodiodes and a photometric front end, configured to receive a reflection of the transmitted light from the user's skin and generate a light intensity signal based on the received reflection. The light intensity signal may be an analog signal that is filtered, processed and converted into a digital PPG signal by the photometric front end of the receiver. In embodiments, the light intensity signal is processed and digitized into a PPG signal by a processor of the monitoring device directly or by controlling circuitry, such as the photometric front end.

Figure 7:
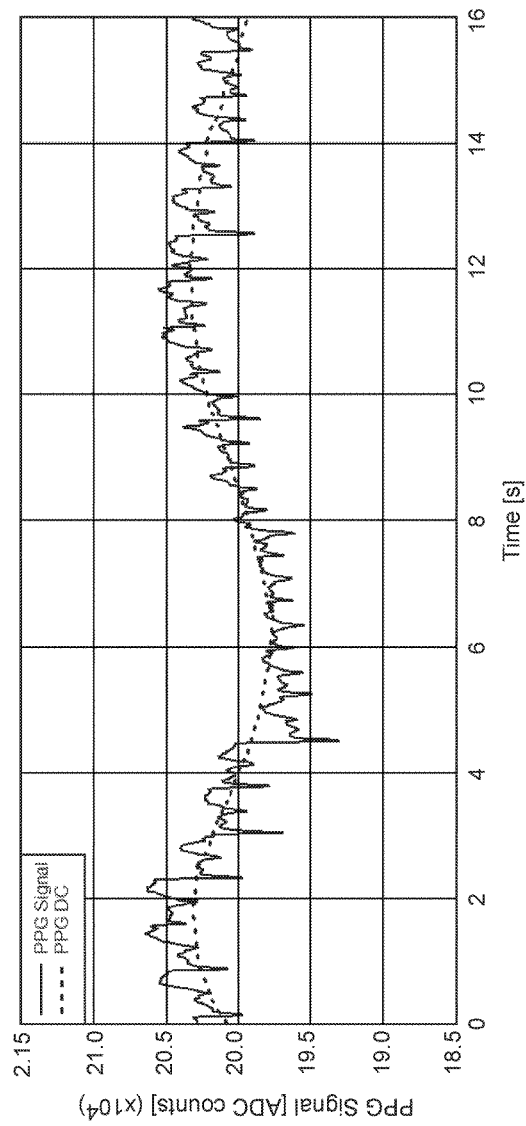
FIG. 7 is a graph of a PPG signal generated by a photometric front end circuit of a fitness monitor while the fitness monitor is worn by a user.

A processor of the monitoring device controls the amount of light output by one or more emitters (e.g., LEDs) by selecting an intensity level for the emitters based on a comparison of a determined DC component of a PPG signal and a stored reference value. A selected intensity level may include of one of more sample-configuration parameters including, for instance, peak pulse current, pulse duration, or number of pulses per sample. The processor may determine a DC component of a PPG signal, as illustrated in FIG. 7, provided by a photometric front end circuit by analyzing levels of the PPG signal over a period of time. In embodiments, the processor may determine the average of PPG signal levels over a period of time as the DC component of the PPG signal. The monitoring device may utilize the reference value based on the variability of the PPG signal, which is generated by an analog front end during an idle state of the monitoring device, to improve or maintain the signal quality of the PPG signal enables determination of a cardiac component that may be used to determine an accurate heart rate for the user and/or reduce power consumption of the fitness device. The signal quality of the PPG signal may be associated with a noise power of the PPG signal and other signal-path components of the monitoring device.

Figure 1:
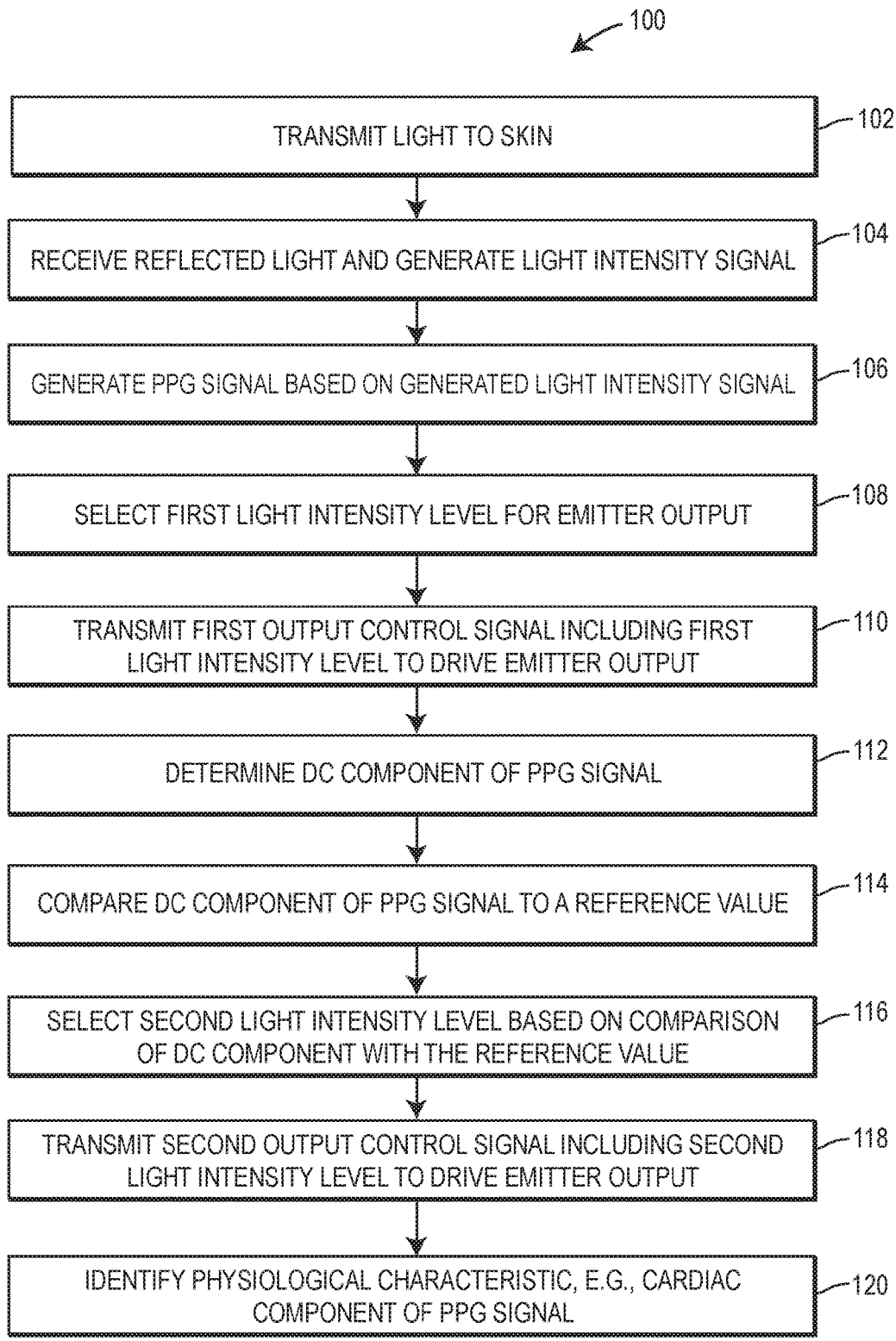
FIG. 1 depicts an exemplary process for operating a fitness monitor for monitoring a physiological characteristic of a user as described herein.

FIG. 1 depicts a block diagram of an exemplary process 100 for improving the accuracy of and/or minimizing the power consumed by a monitoring device, a fitness monitor, for measuring a physiological characteristic of an individual. The fitness monitor includes one or more processors and transmits light toward the skin of an individual (block 102) to facilitate identification of a physiological characteristic within a generated photoplethysmogram (PPG) signal (block 120). The physiological characteristic may be a cardiac component of the PPG signal. An emitter and emitter driver are configured to transmit light having one of a variety of selectable intensity levels.

A receiver of the fitness monitor receives a reflection of the transmitted light and generates an analog light intensity signal based on the received light (block 104). Photometric front end circuitry receives the analog light intensity signal, filters the signal and generates a digital PPG signal based on the received light intensity signal (block 106). The PPG signal includes information associated with a physiological characteristic of the individual. For example, a cardiac component of the PPG signal may provide a user's heartbeat signal.

One or more processors of the fitness monitor are configured to select a first intensity level for the emitter to output light (block 108) and transmit a first output control signal to the emitter driver, to cause the emitter to output light at the selected first intensity level (block 110). The one or more processors determine a DC component of the PPG signal (block 112) and a second intensity level is selected (block 116) based on a comparison of the determined DC component with a reference value (block 114).

The one or more processors of the fitness monitor transmit a second output control signal including the selected second light intensity level to the emitter driver to cause the emitter to output light (block 118) at the selected second intensity level. In embodiments, the selected second light intensity level may cause a PPG signal having a DC component determined to be lower than desired, based on a comparison of the DC component with the stored reference value, to be increased to a level that enables determination of a cardiac component that may be used to determine an accurate heart rate for the user. Similarly, the selected second light intensity level may cause a PPG signal having a DC component determined to be greater than desired, based on a comparison of the DC component with the stored reference value, to be reduced to a level that enables determination of a cardiac component that may be used to determine an accurate heart rate for the user while reducing consumed power.

The one or more stored reference values characterize performance of the fitness monitor independent of its use by an individual. Rather, a reference value is determined for the fitness monitor based on at least one configuration of one or more components of the fitness monitor at a time when the fitness monitor is not proximate to the skin of a user. Subsequently, the processor may utilize the stored reference value to dynamically alter operation of the one or more components of the fitness monitor when the device is being used by a user (the fitness monitor is now proximate to the skin of the user) to acquire a PPG signal having adequate signal quality and/or reduced power consumption.

This dynamic configuration of one or more fitness monitor components accounts for variations in operating parameters of the device and biometric characteristics of the user without utilizing an operating mode that characterizes the user while the device is worn by the user. For example, a selected second light intensity level may cause a PPG signal having a DC component determined to be lower than desired due to selected operating parameters of the device and/or one or more biometric characteristics of a user to be increased to a level that enables determination of a cardiac component. Biometric characteristics that may require the light intensity level to be increased may include such as a darker skin tone or complexion of the user, high body fat of the user, increased moisture level of the user's skin, high hair density or dark hair color of the user at a location on the user's body against which the monitoring device is positioned to output light and receive reflections. The processor may determine that the light intensity level must be increased based on a comparison of the DC component with the stored reference value that characterized performance of the fitness monitor independent of its use by an individual.

Figure 2:
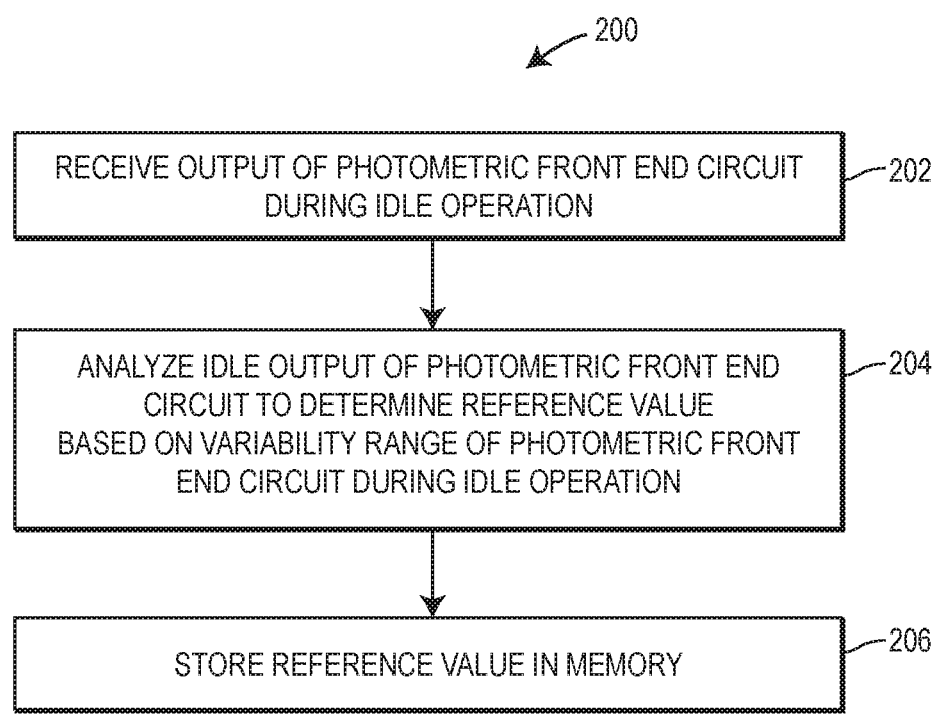
FIG. 2 depicts a portion of an exemplary process for determining the reference value used for the comparison with the determined DC component of the PPG signal as described herein.

FIG. 2 depicts a block diagram of an exemplary process 200 for determining the reference value used by the processor in the comparison with the determined DC component of the PPG signal, referred to at block 114 of FIG. 1. An exemplary PPG signal and DC component of the PPG signal is illustrated in FIG. 7. One or more reference values may be determined by the processor of the fitness monitor when the fitness monitor is not worn by or otherwise in use by a user (e.g., prior to the intended operation of the fitness monitor) in one or more configurations of the fitness monitor to characterize performance of the fitness monitor independent of its use by an individual.

In embodiments, the techniques disclosed herein for determining one or more reference values may be implemented after initial use by a user during any moment when the fitness monitor is not being worn by a user. For example, the reference value may be determined based on the PPG signal output by the photometric front end circuitry when the fitness monitor is not being worn by a user and has been placed on a table (for storage or charging of the fitness monitor). In embodiments, the one or more processors of the fitness monitor may utilize a signal from an inertial sensor and/or a received PPG signal to automatically determine that the device is not being worn by a user and then initiate determination of one or more reference values for storage in the memory device of the fitness monitor. In embodiments, the processor of the fitness device may account for any ambient light received by photodiodes of the fitness device when the device is not in a controlled environment having a known amount of light.

The processor of the fitness monitor may compare a stored reference value with a recently determined reference value to determine whether both reference values should be retained or whether only one of the reference values should continue to be stored. For example, the memory device of the fitness monitor may include a data table providing a reference value for a plurality of configurations of one or more components of the fitness monitor, each reference value determined at a time when the fitness monitor is not proximate to the skin of a user. For instance, the data table may provide the processor of the fitness device a reference value for particular configuration of operating parameters of the device (e.g., a particular gain setting, number of channels for one or more photodiodes, a number of pulses of light output by one or more emitters (LEDs), a width of each pulse output by the one or more emitters (LEDs), a voltage of the one or more emitters (LEDs), a current of the one or more emitters (LEDs), etc.).

Determination of one or more reference values in an idle state or condition of the fitness monitor may occur at any moment when the fitness monitor is not being worn by a user. For example, the photodiodes of the fitness monitor may be shielded from light or the fitness monitor may be placed in a dark, light-absorbing room or calibration box before, shortly after, or during the manufacture of the fitness monitor. Alternately, the idle state of the photometric front end circuit may occur after initial use of the fitness monitor by the user at a time when the fitness monitor is not proximate to the skin of the user and is not receiving reflections of the light transmitted by the emitter, the reflections from which are modulated by the user's skin. In embodiments, the fitness monitor may receive reflected light originating from an emitter (e.g., LED) or other sources (e.g., ambient light) and the processor of the fitness monitor may determine the reference value based on the PPG signal output by the photometric front end circuit, provided that the fitness monitor is not worn by a user whose skin the received light passed through.

The one or more processors of the fitness monitor receive the PPG signal output by the photometric front end circuitry during idle operation (block 202), analyze the output of the photometric front end during the idle state to determine a reference value characterizing the fitness monitor based on a determined variability of the PPG signal provided by the photometric front end circuit (block 204), and store the determined reference value in a memory device of the fitness monitor (block 206). The predetermined reference value may be calculated when the one or more photodiodes of the receiver are not receiving reflections of light output by the one or more emitters (e.g., LEDs) or receiving only predictable reflections (for example, from surfaces that are not living tissue) to characterize fitness monitor based on the inherent range of operating characteristics of components utilized to perform the measurements that may affect the accuracy of the monitoring device. In the idle state, the PPG signal output provided by the photometric front end circuit is not in response to, based on, or associated with unpredictable modulation of reflected light originating from the emitter, and thus the output of the photometric front end circuit during the idle state may be considered as an inherent "noise" characteristic, e.g., noise floor or base-level, of the fitness monitor, including the photometric front end circuitry.

In embodiments, reference values may be determined by the processor when one or more components of the fitness monitor are configured to operate in one of a plurality of operating modes that are anticipated to be used when the fitness monitor may be worn and used by a user. For example, the processor of the fitness device may determine a reference value characterizing operation of the fitness device for each gain setting of a transimpedance amplifier (TIA) by collecting PPG signal output by the photometric front end circuitry during idle operation. Similarly, the processor of the fitness device may determine a reference value characterizing operation of the fitness device for varying number of channels (signal paths) between the photometric front end and one or more photodiodes by collecting PPG signal output by the photometric front end circuitry during idle operation. For example, two or more channels may be used to distribute charge from one or more photodiodes amongst the two or more channels to increase dynamic range. Alternatively, the processor of the fitness device may determine a reference value characterizing operation of the fitness device based on varying number of pulses and/or width of pulses output by the LEDs by collecting PPG signal output by the photometric front end circuitry during idle operation. The processor of the fitness device may determine a reference value characterizing operation of the fitness device based on a varying voltage or current of the LEDs by collecting PPG signal output by the photometric front end circuitry during idle operation.

One or more reference values may be stored in memory device of the fitness device corresponding to each configuration of the fitness device. For example, reference values may be determined once for a plurality of fitness devices based on a shared hardware and/or software platform of a fitness device. A sample of one or more fitness devices representative of similar fitness devices may be utilized to determine the reference values for all of the fitness devices. For example, a reference value may be determined as representative of a plurality of fitness devices that share substantially the same hardware and/or software or that share a common component (e.g., a photometric front end circuit, an optical sensing module having one or more LEDs and one or more photodiodes, power supply, etc.). Alternatively, reference values may be independently determined for each fitness device based on the hardware and software platform for each respective fitness device. In embodiments, a memory device of a fitness device may include a combination of reference values determined for a plurality of similar fitness devices and reference values determined for that device. In embodiments, the stored reference values are based on the expected noise levels for the photometric front end circuit and/or optical sensing module.

When the processor compares the determined DC component of the PPG signal with a determined reference value, the processor may retrieve a reference value corresponding to the current configuration of the fitness device to select a second intensity signal. The processor may select a first intensity level for one or more emitters (e.g., LEDs) based on a default intensity level stored in memory.

Figure 3:
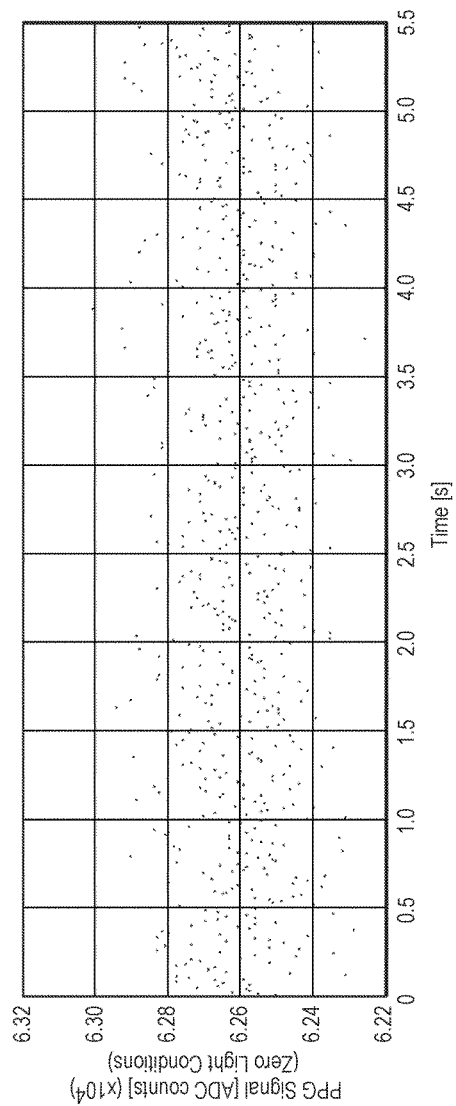
FIG. 3 depicts an example dot-plot graph depicting received signals of the fitness monitor during the idle state as described herein.

FIG. 3 depicts an exemplary dot-plot of a PPG signal output from a photometric front end circuit of the fitness monitor in an idle state (when there is no light input to the photometric front end circuit from one or more photodiodes). Discrete digitized output points of the idle photometric front end circuit are collected over time, e.g., approximately 5.5 seconds, and provide a range of measurement variability or uncertainty in the amplitude of the PPG signal output that may be used to characterize performance of the fitness monitor independent of its use by an individual. In contrast, it may be expected by some that the theoretical PPG signal output in a controlled environment without light that may be received by one or more photodiodes (absence of light) would exhibit a near-zero output level of the PPG signal and/or an output level of the PPG signal that is flat (i.e., all PPG signal values are the same).

Figure 4:
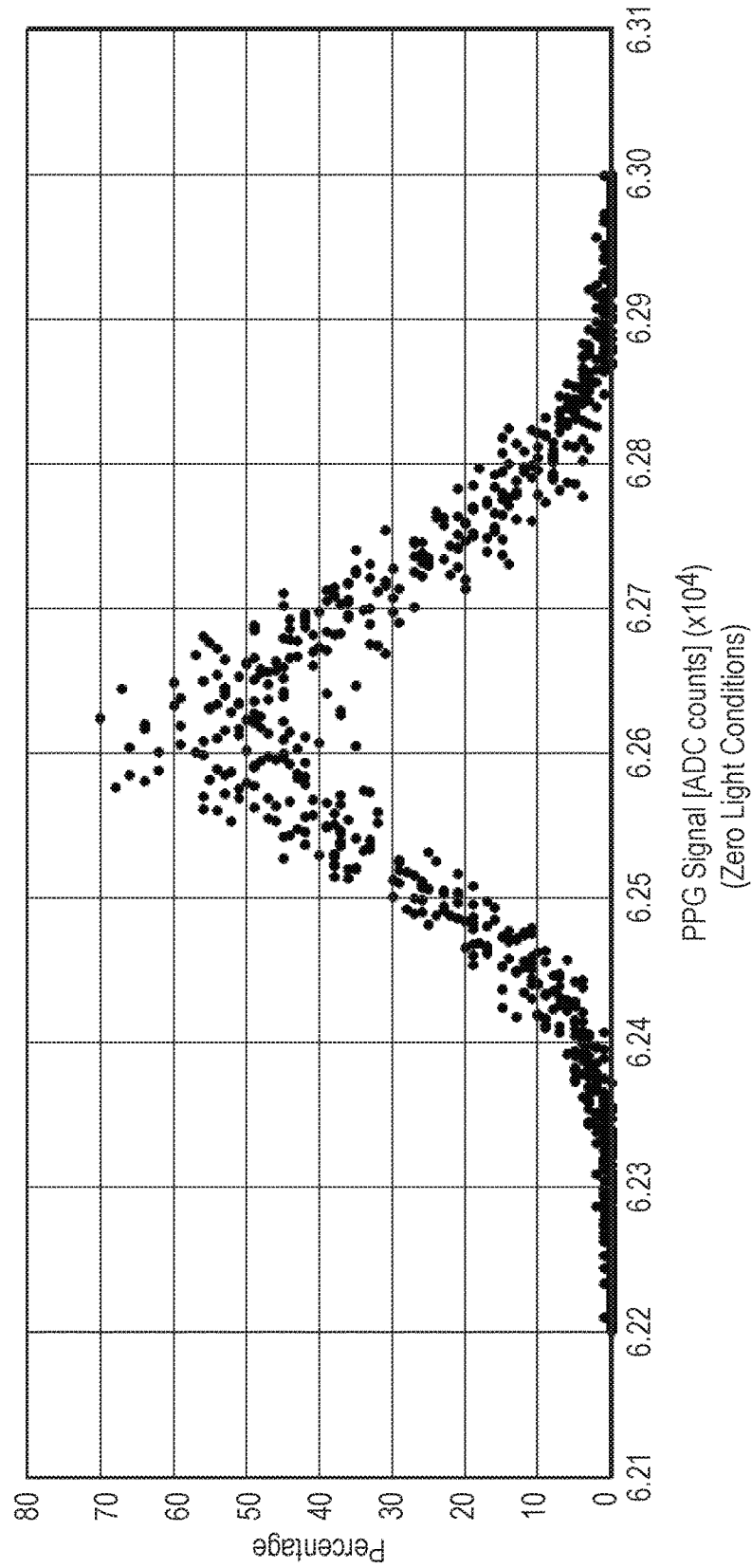
FIG. 4 depicts a Gaussian curve of the data of FIG. 3 relating to the determination of the reference value as described herein.

The reference value characterizing performance of the fitness monitor that may be representative of the range or variability of the PPG signal output from the photometric front end circuit while in the idle state may be determined from empirical and/or statistical analysis of the sampled output of the digitized PPG signal from the idle photometric front end circuit. The statistical analysis may include a normal or Gaussian distribution of the digitized PPG signal output, as shown in FIG. 4. The reference value stored on a memory device internal to and/or external of the fitness monitor may be any mathematical representation of the variation or dispersion of data values. For example, in embodiments, the reference value may be a standard deviation of the PPG signal, a mean value of the PPG signal, a variance of the PPG signal outputs, a root mean square (RMS) of the PPG signal outputs, a peak-to-peak value of the PPG signal outputs, or any combination thereof. The memory device may store a plurality of reference values characterizing performance of the fitness monitor in a plurality of configurations (e.g., different gain settings, numbers of channels for photodiodes, number of pulses, width of pulses, voltage of LEDs, current of the LEDs, etc.). Thus, the memory device may include a table having a determined reference value corresponding to each configuration of the fitness monitor that may be implemented when the fitness monitor is worn and used by a user.

When the processor compares the determined DC component of the PPG signal with a determined reference value, the processor may retrieve a reference value corresponding to the current configuration of the fitness device to select a second intensity signal different from a first intensity signal (e.g., a default LED intensity level). This dynamic configuration of one or more fitness monitor components accounts for variations in operating parameters of the device and biometric characteristics of the user without utilizing an operating mode that characterizes the user while the device is worn by the user. When the fitness monitor is in use, for example, attached to and proximate the skin of a user and monitoring a physiological aspect of the user, the processor may retrieve a reference value characterizing the fitness monitor based on a determined variability or range of the PPG signal provided by the photometric front end circuit, compare a determined DC component of the PPG signal to the reference value and select a light intensity level based on the comparison. For example, a selected second light intensity level may cause a PPG signal having a DC component determined to be lower than desired due to selected operating parameters of the device and/or one or more biometric characteristics of a user to be increased to a level that enables determination of a cardiac component of the PPG signal.

An example embodiment of a fitness monitor 500 capable of executing the methods and processes described above is illustrated in FIG. 5. The fitness monitor 500 includes an application processor 550 further including a user interface module 502, a location determining component 504 (e.g., a global positioning system (GPS) receiver, Assisted-GPS, etc.), a communication module 506, an inertial sensor 508 (e.g., accelerometer, gyroscope, etc.), and a controller 510.

The fitness monitor 500 may be a general-use wearable computer (e.g., a watch, smart glasses, etc.), a cellular phone, a smartphone, a tablet computer, or a mobile personal computer, capable of monitoring a physiological aspect of an individual as described herein. The fitness monitor 500 may be a thin-client device or terminal that sends processing functions to a server device 522 via a network 524. Communication via the network 524 may include any combination of wired and wireless technology. For example, network 524 may include a USB cable between fitness monitor 500 and computing device 548 to facilitate the bi-directional transfer of data between fitness monitor 500 and computing device 544.

Figure 5:
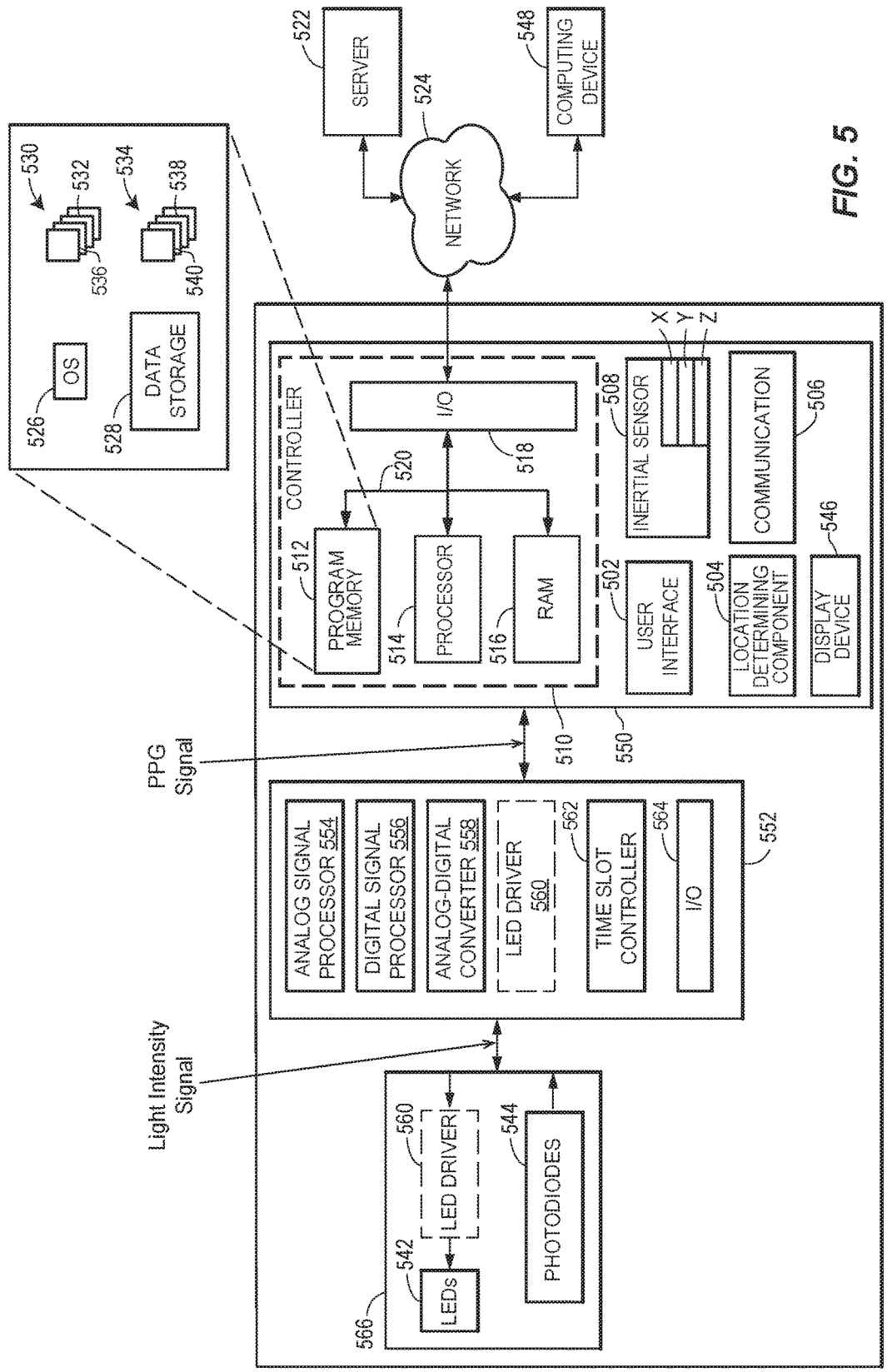
FIG. 5 is a block diagram of a an example embodiment of a fitness monitor for monitoring a physiological characteristic of a user as described herein.

The controller 510 of the application processor 550 may include a program memory 512, a microprocessor (MP) 514, a random-access memory (RAM) 516, and an input/output (I/O) circuitry 518, all of which may be communicatively interconnected via an address/data bus 520. Although the I/O circuitry 518 is depicted in FIG. 5 as a single block, the I/O circuitry 518 may include a number of different types of I/O circuits. The program memory 512 may include an operating system 526, a data storage device 528, a plurality of software applications 530, and/or a plurality of software routines 534. The operating system 526 of program memory 512 may include any of a plurality of mobile platforms, such as the iOS®, Android™, Palm® webOS, Windows® Mobile/Phone, BlackBerry® OS, or Symbian® OS mobile technology platforms, developed by Apple Inc., Google Inc., Palm Inc. (now Hewlett-Packard Company), Microsoft Corporation, Research in Motion (RIM), and Nokia, respectively. The data storage device 528 of program memory 512 may include application data for the plurality of applications 530, routine data for the plurality of routines 534, and other data necessary to interact with the server 522 through the network 524.

In particular, the data storage device 528 may include one or more reference values characterizing performance of the fitness monitor representative of the range of variability of the PPG signal output from the photometric front end circuit while in the idle state of the fitness monitor 500 (e.g., PPG signal output in response to a zero light input). Additional data stored within the data storage device 528 may include cardiac component data associated with one or more other individuals who wear and use of the fitness monitor 500. The cardiac component data may include one or more compilations of recorded physiological aspects of the user, including, but not limited to, a heartbeat, heart rate, heart-rate variability, speed, distance traveled, calculating calories burned, body temperature, and the like. In some embodiments, the controller 510 may also include, or otherwise be operatively coupled for communication with other data storage mechanisms (e.g., one or more hard disk drives, optical storage drives, solid state storage devices, etc.) that may reside within the fitness monitor 500 and/or operatively coupled to the network 524 and/or server device 522.

The fitness monitor 500 further includes a photometric front end circuit 552 communicably coupled between the application processor 550 and an optical sensing module 566. The optical sensing module 566 includes one or more LEDs 542 and one or more photodiodes 544, and is configured for placement adjacent the skin of a user when the fitness device 500 is secured or attached to the user. The photometric front end 552 may include an analog signal processor 554, a digital signal processor 556, an analog-to-digital converter 558, a time slot controller 562, I/O circuitry 562, and one or more LED drivers 560 causing the LED(s) 542 to output light at one of a plurality of intensity levels. In embodiments, the LED driver 560 may alternately be integrated within the optical sensing module 566 as indicated by the dotted lines of the component. Further still, the LEDs 542, LED driver 560, and the photodiodes 544 may be integrated within the photometric front end 552.

Operation of the photometric front end 552 facilitates stimulating the LED(s) 542 and measuring reflections of the light from the user's skin using one or more photodiodes 544. The reflected signals may be output by the photodiodes 544 as a light intensity signal analyzed and filtered by the analog signal processor 554, digitized by the analog-to-digital converter 558, and analyzed by the digital signal processor 556. Control and/or data communication amongst the application processor 550, photometric front end 552, and optical sensing module 566 is facilitated via the I/O circuitry 564. In embodiments, any signals provided by the photometric front end 552 or optical sensing module 566 or any information determined based on such signals may be stored in the data storage 526 of the application processor 550.

The LEDs (e.g., emitters) 542 output visible and/or non-visible light, and one or more photodiodes (e.g., receivers) 544 receive the visible and/or non-visible light and generate a light intensity signal based on the received reflections of the electromagnetic radiation. For example, LEDs 542 may include any combination of green light-emitting diodes (LEDs), red LEDs, and/or infrared LEDs that emit light into the user's skin. The photodiodes 544 receive reflections of visible-light and/or infrared (IR) light output by the LEDs 542 into the user's skin and generate the light intensity signal based on the received reflection. The light intensity signals generated by the one or more photodiodes 544 may be communicated to the photometric front end 552 for signal processing and digitization. The photometric front end 552 may include filters for the light intensity signals and analog-to-digital converters to digitize the light intensity signals into PPG signals including a cardiac cycle signal component associated with the user's heartbeat.

Typically, the one or more LEDs 542 are positioned against the user's skin to emit light into the user's skin and the one or more photodiodes 544 are positioned near the LEDs 542 to receive light emitted by the one or more emitters 542 after reflection from the user's skin. The photometric front end 552 and/or the processor 514 of fitness monitor 500 may determine a PPG signal based on a light intensity signal output by one or more photodiodes 544 based on light reflected after transmission of the light through or reflection from the user's skin that has been received by the photodiodes 544.

The photometric front end 552 may utilize multiple time slots during operation, wherein the time slot controller 562 coordinates sequential operation of the signal path from LED stimulation to data capture and processing for each time slot and desired sampling period.

In both the transmitted and reflected uses, the intensity of measured light may be modulated by the cardiac cycle due to variation in tissue blood perfusion during the cardiac cycle. In activity environments, the intensity of measured light may also be strongly influenced by many other factors, including, but not limited to, the inherent "noise" characteristic static and/or variable ambient light intensity, body motion at the measurement location, static and/or variable sensor pressure on the skin, motion of the sensor relative to the body at the measurement location, breathing, and/or light barriers (including hair, opaque skin layers, sweat, etc.). Relative to these sources, the cardiac cycle component of the PPG signal can be very weak, frequently by one or more orders of magnitude.

The location determining component 504 may be a GPS receiver that is configured to provide geographic location information of the fitness monitor 500. The location determining component may be, for example, a GPS receiver such as those provided in various products by GARMIN®. Generally, GPS is a satellite-based radio navigation system capable of determining continuous position, velocity, time, and direction information. Multiple users may simultaneously utilize GPS. GPS incorporates a plurality of GPS satellites that orbit the earth. Based on these orbits, GPS satellites can relay their location to a GPS receiver. For example, upon receiving a GPS signal, e.g., a radio signal, from a GPS satellite, the fitness monitor 500 disclosed herein can determine a location of that satellite. The fitness monitor 500 can continue scanning for GPS signals until it has acquired a number, e.g., at least three, of different GPS satellite signals. The fitness monitor 500 may employ geometrical triangulation, e.g., where the watch utilizes the known GPS satellite positions to determine a position of the fitness monitor 500 relative to the GPS satellites. Geographic location information and/or velocity information can be updated, e.g., in real time on a continuous basis, for the fitness monitor 500.

In embodiments, inertial sensor 508 may incorporate one or more accelerometers positioned to determine the acceleration and direction of movements of fitness monitor 500. The accelerometer may determine magnitudes of acceleration in an X-axis, a Y-axis, and a Z-axis to measure the acceleration and direction of movement of fitness monitor 500 in each respective direction (or plane). It will be appreciated by those of ordinary skill in the art that a three dimensional vector describing a movement of the fitness monitor 500 through three dimensional space can be established by combining the outputs of the X-axis, Y-axis, and Z-axis accelerometers using known methods. Single and multiple axis models of the inertial sensor 508 are capable of detecting magnitude and direction of acceleration as a vector quantity, and may be used to sense orientation and/or coordinate acceleration of the user.

The photodiodes 544, location determining component 504 and the inertial sensors 508 may be referred to collectively as the "sensors" of the fitness monitor 500. It is also to be appreciated that additional location determining components 504 and/or inertial sensor(s) 508 may be operatively coupled to the fitness monitor 500. In embodiments, the fitness monitor 500 may also include or be coupled to a microphone incorporated with the user interface module 502 and used to receive voice inputs from the user while the fitness monitor 500 monitors a cardiac signal of a user and determines physiological information based on the cardiac signal.

The communication module 506 may communicate with computing device 544 and/or server device 522 via any suitable wired or wireless communication protocol independently or using I/O circuitry 518. The wired or wireless network 524 may include a wireless telephony network (e.g., GSM, CDMA, LTE, etc.), one or more standard of the Institute of Electrical and Electronics Engineers (IEEE), such as 802.11 or 802.16 (Wi-Max) standards, Wi-Fi standards promulgated by the Wi-Fi Alliance, Bluetooth standards promulgated by the Bluetooth Special Interest Group, a near field communication standard (e.g., ISO/IEC 18092, standards provided by the NFC Forum, etc.), and so on. Wired communications are also contemplated such as through universal serial bus (USB), Ethernet, serial connections, and so forth.

The fitness monitor 500 may be configured to communicate via one or more networks 524 with a cellular provider and an Internet provider to receive mobile phone service and various content, respectively. Content may represent a variety of different content, examples of which include, but are not limited to: map data, which may include route information; web pages; services; music; photographs; video; email service; instant messaging; device drivers; real-time and/or historical weather data; instruction updates; and so forth.

The user interface 502 of the fitness monitor 500 may include a "soft" keyboard that is presented on a display screen of the fitness monitor 500, an external hardware keyboard communicating via a wired or a wireless connection (e.g., a Bluetooth keyboard), and/or an external mouse, or any other suitable user-input device or component. As described earlier, the user interface 502 may also include or communicate with a microphone capable of receiving voice input from a vehicle operator as well as a display device 546 having a touch input.

With reference to the controller 510, it should be appreciated that controller 510 may include multiple microprocessors 514, multiple RAMs 516, and multiple program memories 512. The controller 510 may implement the RAM 516 and the program memories 512 as semiconductor memories, magnetically readable memories, and/or optically readable memories, for example. The one or more processors 514 may be adapted and configured to execute any of the plurality of software applications 530 and/or any of the plurality of software routines 534 residing in the program memory 512, in addition to other software applications. One of the plurality of applications 530 may be a client application 532 that may be implemented as a series of machine-readable instructions for performing the various functions associated with implementing the performance monitoring system as well as receiving information at, displaying information on, and transmitting information from the fitness monitor 500. The client application 532 may function to implement a system wherein the front-end components communicate and cooperate with back-end components as described above. The client application 532 may include machine-readable instructions for implementing the user interface 502 to allow a user to input commands to, and receive information from, the fitness monitor 500. One of the plurality of applications 530 may be a native web browser 536, such as Apple's Safari®, Google Android™ mobile web browser, Microsoft Internet Explorer® for Mobile, Opera Mobile™, that may be implemented as a series of machine-readable instructions for receiving, interpreting, and displaying web page information from the server device 522 or other back-end components while also receiving inputs from the fitness monitor 500. Another application of the plurality of applications 530 may include an embedded web browser 542 that may be implemented as a series of machine-readable instructions for receiving, interpreting, and displaying web page information from the server device 522 or other back-end components within the client application 532.

The client applications 530 or routines 534 may include one or more processes for determining one or more reference value(s) associated with the non-ideal operating characteristics of the fitness monitor 500. Namely, the analysis and determination of the reference values based on the output values of the PPG signal provided by the optical sensing module 566 in a controlled environment (e.g., no light is received by the photodiodes 544) during the idle state of the fitness monitor 500.

The client applications 530 or routines 534 may further include an accelerometer routine 538 that determines the acceleration and direction of movements of the fitness monitor 500, which correlate to the acceleration, direction, and movement of the user. The accelerometer routine 538 may receive and process data from the inertial sensor 508 to determine one or more vectors describing the motion of the user for use with the client application 532. In some embodiments where the inertial sensor 508 includes an accelerometer having X-axis, Y-axis, and Z-axis accelerometers, the accelerometer routine 538 may combine the data from each accelerometer to establish the vectors describing the motion of the user through three dimensional space. In some embodiments, the accelerometer routine 538 may use data pertaining to less than three axes.

The client applications 530 or routines 534 may further include a velocity routine 540 that coordinates with the location determining component 504 to determine or obtain velocity and direction information for use with one or more of the plurality of applications, such as the client application 532, or for use with other routines.

The user may also launch or instantiate any other suitable user interface application (e.g., the native web browser 536, or any other one of the plurality of software applications 530) to access the server device 522 to implement the monitoring process. Additionally, the user may launch the client application 532 from the fitness monitor 500 to access the server device 522 to implement the monitoring process.

After data has been gathered or determined by the sensors of the fitness monitor 500, processor 514 may utilize a stored reference value to select (and thereby adjust) an intensity level for one or more emitters (e.g., LEDs) to improve or maintain the signal quality of the PPG signal enables determination of a cardiac component that may be used to determine an accurate heart rate for the user of fitness monitor 500 and/or reduction of power consumed by the fitness monitor 500. The fitness monitor 500 may also implement time, frequency, pre-conditioning and post-conditioning, and time-variant filtering techniques as described in simultaneously filed U.S. patent application Ser. No. 15/296,956, entitled, "HEART RATE MONITOR WITH TIME-VARYING LINEAR FILTERING"; the contents of which are expressly incorporated herein by reference. Once the extent of the adjustment has been assessed, a cardiac signal can be determined. The fitness monitor 500 may also transmit information associated with the cardiac component of the user. For example, the transmitted information may be sent to a fitness facility capable of analyzing the data.

After data has been gathered or determined by the sensors of the fitness monitor 500, previously acquired data may be utilized to determine the extent of adjustment to the time-variant filters. Once the extent of the adjustment has been assessed, a cardiac signal can be determined. The fitness monitor 500 may also transmit information associated with the cardiac component of the user. For example, the transmitted information may be sent to a fitness facility capable of analyzing the data.

In embodiments where the fitness monitor 500 is a thin-client device, the server device 522 may perform one or more processing functions remotely that may otherwise be performed by the fitness monitor 500. In such embodiments, the server device 522 may include a number of software applications capable of receiving user information gathered by the sensors to be used in determining the cardiac component of the user. For example, the fitness monitor 500 may gather information from its sensors as described herein, but instead of using the information locally, the fitness monitor 500 may send the information to the server device 522 for remote processing. The server device 522 may perform the analysis of the gathered user information to determine a fitness aspect of the user as described herein. The server device 522 may also transmit information associated with the cardiac component of the user. For example, the information transmitted by the server device 522 may be sent to a fitness facility and include a request for analysis.

Figure 6A:
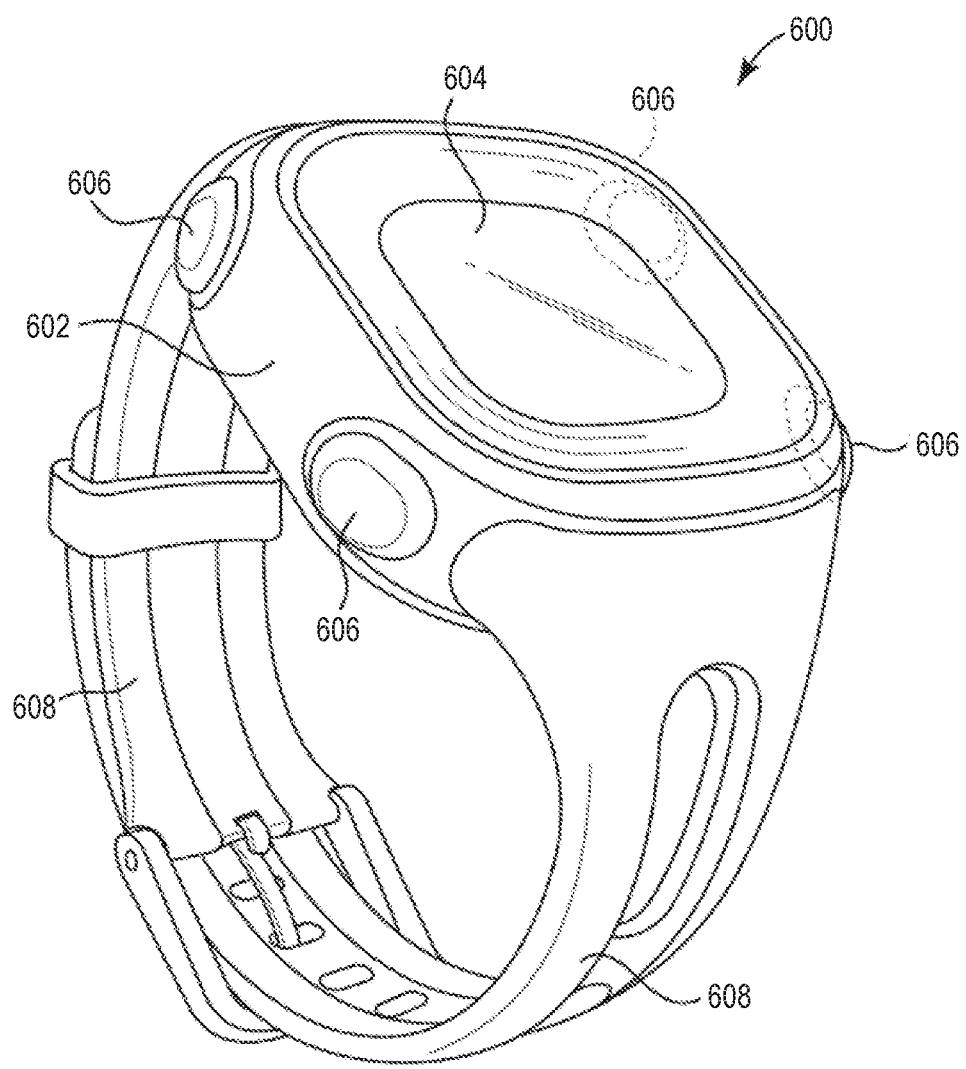
FIGS. 6A and 6B are illustrations depicting one embodiment of the fitness monitor for monitoring one or more physiological and/or performance characteristics of a user as described herein.
Figure 6B:
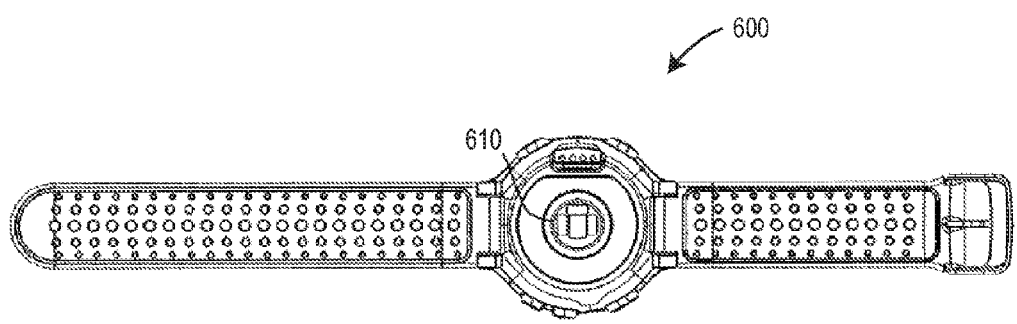

FIGS. 6A and 6B illustrate views of one example embodiment of the fitness monitor in accordance with one or more aspects described herein. The fitness monitor 600 described above may be configured in a variety of ways to determine and provide fitness information, including one or more cardiac components, as well as navigation functionality to the user of the device 600. For instance, fitness monitor 600 includes a housing 602 of a sports watch or a pedometer including a processor configured for use during fitness and/or sporting activities. It is contemplated, however, that the disclosed techniques may be implemented in a mobile phone, a hand-held portable computer, a tablet computer, a personal digital assistant, a multimedia device, a media player, a game device, any combination thereof, and so forth.

The fitness monitor 600 includes a case or housing 602 configured to house, e.g., substantially enclose, various components of the fitness monitor 600. The housing 602 may be formed from a lightweight and impact-resistant material such as plastic, nylon, or combinations thereof, for example. The housing 602 may be formed from a non-conductive material, such a non-metal material, for example. The housing 602 may include one or more gaskets, e.g., a seal, to make it substantially waterproof or water resistant. The housing 602 may include a location for a battery and/or another power source for powering one or more components of the fitness monitor 600. The housing 602 may be a singular piece or may include a plurality of sections. In some embodiments, the housing 602 may be formed from a conductive material, such as metal, or a semi-conductive material.

The fitness monitor 600 includes a display device 604. The display device 604 may include a liquid crystal display (LCD), a thin film transistor (TFT), a light-emitting diode (LED), a light-emitting polymer (LEP), and/or a polymer light-emitting diode (PLED). The display device 604 may be capable of displaying text and/or graphical information. The display device 604 may be backlit such that it may be viewed in the dark or other low-light environments. One example embodiment of the display device 604 is a 100 pixel by 64 pixel film compensated super-twisted nematic display (FSTN) including a bright white light-emitting diode (LED) backlight. The display device 604 may include a transparent lens that covers and/or protects components of the fitness monitor 600. The display device 604 may be provided with a touch screen to receive input (e.g., data, commands, etc.) from a user. For example, a user may operate the fitness monitor 600 by touching the touch screen and/or by performing gestures on the screen. In some embodiments, the touch screen may be a capacitive touch screen, a resistive touch screen, an infrared touch screen, combinations thereof, and the like. The fitness monitor 600 may further include one or more input/output (I/O) devices (e.g., a keypad, buttons, a wireless input device, a thumbwheel input device, a trackstick input device, and so on). The I/O devices may include one or more audio I/O devices, such as a microphone, speakers, and so on.

In accordance with one or more embodiments of the present disclosure, the fitness monitor 600 includes a user interface with one or more control buttons 606. As illustrated in FIG. 6A, four control button 606 are associated with, e.g., adjacent, the housing 602. While FIG. 6A illustrates four control buttons 606 associated with the housing 602, it is to be understood that the fitness monitor 600 may include more or less control buttons 606. Each control button 606 is configured to generally control a function of the fitness monitor 600. Functions of the mobile electronic device 600 may be associated with a location determining component and/or a performance monitoring component. Functions of the fitness monitor 600 may include, but are not limited to, displaying a current geographic location of the fitness monitor 600, mapping a location on the display 604, locating a desired location and displaying the desired location on the display 604, and presenting information based on a cardiac component of the PPG signal including, but not limited to, a cardiac cycle signal, a heartbeat signal, a heart-rate signal or variability of a heart rate signal for the user. User input may be provided from movement of the housing 602, for example, an inertial sensor(s), e.g., accelerometer, may be used to identify vertical, horizontal, and/or angular movement of the housing 602. In addition or alternately, user input may be provided from touch inputs identified using various touch sensing technologies, such as resistive touch or capacitive touch interfaces.

The fitness monitor 600 also includes an optical sensing module 610, as shown in FIG. 6B, including one or more emitters (e.g., LEDs) of visible and/or non-visible light and one or more receivers (e.g., photodiodes) of visible and/or non-visible light that generate a light intensity signal based on the received reflection of light.

The fitness monitor 600 includes a strap 608 that enables one or more LEDs and one or more photodiodes to be securely placed against the skin of a user. The strap 608 is associated with, e.g., coupled to and/or integrated with, the housing 602 and may be removably secured to the housing 602 via attachment of securing elements to corresponding connecting elements. Some examples of securing elements and/or connecting elements include, but are not limited to, hooks, latches, clamps, snaps, and the like. The strap 608 may be made of a lightweight and resilient thermoplastic elastomer and/or a fabric, for example, such that the strap 608 may encircle a portion of a user without discomfort while securing the fitness monitor to the user. The strap 608 may be configured to attach to various portions of a user, such as a user's leg, waist, wrist, forearm, and/or upper arm.

The processor of the fitness monitor may periodically determine a DC component of a received PPG signal. In other words, the processor continuously determines whether a different light intensity level must be selected based on a comparison of the determined DC component with a stored reference value. As illustrated in FIG. 7, a PPG signal provided by a photometric front end of the fitness device includes a cardiac component and the levels of the PPG signal may vary over a period of time. In addition to changes between peak-to-peak levels of the cardiac component of the PPG signal, the DC component (illustrated with a broken line) may vary significantly due to movement of the fitness device (caused by movement of the user's arm) or other factors. In some embodiments, the DC component of the PPG signal is determined by the processor to be a simple average or a moving average of PPG signal levels over a period of time. For example, for PPG signal illustrated in FIG. 7, the processor may determine an average of the various PPG signal levels over a period of sixteen seconds or a different duration (e.g., 2 seconds, 8 seconds, etc.). Other techniques, such as utilization of low-pass filtering, may be implemented to determine the DC component of the PPG signal.

The comparison of the determined DC component of the PPG signal to a stored reference value, which may correspond to a variance associated with a current configuration of one or more components, by processor may include determining a mathematical difference between or ratio of the values. In embodiments, the memory device may store a predetermined range of acceptable differences or ratios that do not require selection of a second intensity level based on the comparison. For example, if the determined DC component is determined to have an acceptable amount of variation, the processor of the fitness device may continue to use a selected first intensity level (e.g., default intensity level, a previously determined intensity level, etc.) without modification.

The applications and benefits of the systems, methods, and techniques described herein are not limited to only the above examples. Many other applications and benefits are possible by using the systems, methods, and techniques described herein. Thus, many modifications and variations may be made in the techniques and structures described and illustrated herein without departing from the spirit and scope of the present invention. Accordingly, it should be understood that the methods and apparatus described herein are illustrative only and are not limiting upon the scope of the invention.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Also, unless a claim element is defined by reciting the word "means" and a function without the recital of any structure, it is not intended that the scope of any claim element be interpreted based on the application of 35 U.S.C. §112(f) and/or pre-AIA 35 U.S.C. §112, sixth paragraph.

Moreover, although the foregoing text sets forth a detailed description of numerous different embodiments, it should be understood that the scope of the patent is defined by the words of the claims set forth at the end of this patent. The detailed description is to be construed as exemplary only and does not describe every possible embodiment because describing every possible embodiment would be impractical, if not impossible. Numerous alternative embodiments could be implemented, using either current technology or technology developed after the filing date of this patent, which would still fall within the scope of the claims.

What is claimed is:

1. A fitness monitor for monitoring a cardiac signal of a user, the device comprising:
   an emitter configured to output light toward skin of the user;
   an emitter driver configured to cause the emitter to output light at one of a plurality of intensity levels;
   a receiver configured to receive a reflection of the transmitted light and generate a light intensity signal based on the received reflection;
   a photometric front end configured to receive the light intensity signal and generate a photoplethysmogram (PPG) signal based on the light intensity signal, the PPG signal including a cardiac signal of the user;
   a memory device configured to store a reference value characterizing performance of the photometric front end based on a variability of the PPG signal output from the photometric front end during idle operation; and
   a processor communicatively coupled to the emitter, the receiver, photometric front end and the memory device, the processor configured to:
      select a first intensity level for the emitter to output light,
      transmit a first output control signal including the selected first intensity level to the emitter driver causing the emitter to output light at the selected first intensity level,
      determine a DC component of a PPG signal received from photometric front end,
      select a second intensity level based on a comparison of the determined DC component of the received PPG signal with the stored reference value,
      transmit a second output control signal including the selected second intensity level to the emitter driver causing the emitter to output light at the selected second intensity level, and
      identify the cardiac component in the received PPG signal.

2. The fitness monitor of claim 1, wherein the emitter driver is integrated within the photometric front end.

3. The fitness monitor of claim 1, wherein the photometric front end is integrated within the processor.

4. The fitness monitor of claim 1, wherein the emitter is a LED and the receiver is a photodiode.

5. The fitness monitor of claim 1, wherein the processor is further configured to transmit a receiver control signal to the receiver causing the receiver to generate the light intensity signal.

6. The fitness monitor of claim 1, wherein the processor is further configured to transmit a receive timing signal to the photometric front end causing the photometric front end to receive the light intensity signal from the receiver.

7. The fitness monitor of claim 6, wherein the processor is further configured to cause the photometric front end to receive the light intensity signal in a first time period and a second time period based on the receive timing signal.

8. The fitness monitor of claim 1, wherein the first output control signal causes the emitter to output light in a first time period and a second output control signal causes the emitter to output light in the second time period.

9. The fitness monitor of claim 1, wherein the variability of the PPG signal output from the photometric front end during idle operation is determined when the receiver does not receive a reflection of the transmitted light.

10. The fitness monitor of claim 1, wherein the variability of the PPG signal output from the photometric front end during idle operation is a mathematical representation of a variation of the PPG signal measurements.

11. The fitness monitor of claim 1, wherein the reference value is determined when the fitness monitor is not proximate to the skin of the user.

12. The fitness monitor of claim 1, further comprising an inertial sensor configured to provide a motion signal based on sensed movement of the fitness monitor, wherein the processor is further configured to transmit the second output control signal when the motion signal is below a predetermined motion level.

13. A fitness monitor for monitoring a cardiac signal of a user, the device comprising:
   an emitter configured to output light toward skin of the user;
   an emitter driver configured to cause the emitter to output light at one of a plurality of intensity levels;
   a receiver configured to receive a reflection of the transmitted light and generate a light intensity signal based on the received reflection;
   a photometric front end configured to receive the light intensity signal and generate a photoplethysmogram (PPG) signal based on the light intensity signal, the PPG signal including a cardiac signal;
   a reference value characterizing performance of the photometric front end based on a variability of the PPG signal output from the photometric front end when the fitness monitor is not proximate to the skin of the user;

a memory device configured to store the reference value; and a processor communicatively coupled to the emitter, the receiver, photometric front end and the memory device, the processor configured to:

select a first intensity level for the emitter to output light, transmit a first output control signal including the selected first intensity level to the emitter driver causing the emitter to output light at the selected first intensity level, determine a DC component of a PPG signal received from the photometric front end, select a second intensity level based on a comparison of the determined DC component of the received PPG signal with the stored reference value, transmit a second output control signal including the selected second intensity level to the emitter driver causing the emitter to output light at the selected second intensity level, and identify the cardiac component in the received PPG signal.

14. The fitness monitor of claim 13, wherein the emitter driver is integrated within the photometric front end.

15. The fitness monitor of claim 13, wherein the photometric front end is integrated within the processor.

16. The fitness monitor of claim 13, wherein the emitter is a LED and the receiver is a photodiode.

17. The fitness monitor of claim 13, wherein the processor is further configured to transmit a receiver control signal to the receiver causing the receiver to generate the light intensity signal.

18. The fitness monitor of claim 13, wherein the processor is further configured to transmit a receive timing signal to the photometric front end causing the photometric front end to receive the light intensity signal from the receiver.

19. The fitness monitor of claim 18, wherein the processor is further configured to cause the photometric front end to receive the light intensity signal in a first time period and a second time period based on the receive timing signal.

20. A fitness monitor for monitoring a cardiac signal of a user comprising an emitter configured to output light toward skin of the user, an emitter driver configured to cause the emitter to output light at one of a plurality of intensity levels, a receiver configured to receive a reflection of the transmitted light and generate a light intensity signal based on the received reflection, a photometric front end configured to receive the light intensity signal and generate a photoplethysmogram (PPG) signal based on the light intensity signal and representing the cardiac signal, and a tangible non-transitory computer-readable medium storing instructions and a reference value characterizing performance of the photometric front end based on a variability of the PPG signal output from the photometric front end during idle operation, wherein the instructions, when executed by one or more processors, cause the fitness monitor to:

select a first intensity level for the emitter to output light, transmit a first output control signal including the selected first intensity level to the emitter driver causing the emitter to output light at the selected first intensity level, determine a DC component of the PPG signal, select a second intensity level based on a comparison of the determined DC component of the PPG signal with the stored reference value, transmit a second output control signal including the selected second intensity level to the emitter driver causing the emitter to output light at the selected second intensity level, and identify the cardiac component in the PPG signal.

* * * * *